(12) United States Patent
Fourment et al.

(10) Patent No.: US 8,739,783 B2
(45) Date of Patent: Jun. 3, 2014

(54) FLUID PRODUCT DISPENSING DEVICE

(75) Inventors: Olivier Fourment, Paris (FR); Pascal Bruna, Sotteville les Rouens (FR)

(73) Assignee: Aptar France SAS, Le Neubourg (FR)

( * ) Notice: Subject to any disclaimer, the term of this patent is extended or adjusted under 35 U.S.C. 154(b) by 1604 days.

(21) Appl. No.: 11/667,853

(22) PCT Filed: Nov. 16, 2005

(86) PCT No.: PCT/FR2005/050956
§ 371 (c)(1),
(2), (4) Date: May 16, 2007

(87) PCT Pub. No.: WO2006/054021
PCT Pub. Date: May 26, 2006

(65) Prior Publication Data
US 2007/0295333 A1    Dec. 27, 2007

(30) Foreign Application Priority Data
Nov. 16, 2004   (FR) ..................................... 04 52641

(51) Int. Cl.
*A61M 15/00* (2006.01)
*A61M 16/00* (2006.01)
*B65D 83/04* (2006.01)
*B65D 85/42* (2006.01)

(52) U.S. Cl.
USPC ..................................... 128/203.21; 206/532

(58) Field of Classification Search
USPC ............. 128/203.15, 203.19, 203.12, 203.21, 128/203.23; 206/528, 438, 538, 539, 532
See application file for complete search history.

(56) References Cited

U.S. PATENT DOCUMENTS

| 5,492,112 A | 2/1996 | Mecikalski et al. |
| 6,209,538 B1 * | 4/2001 | Casper et al. ............ 128/203.15 |
| 2002/0134382 A1 * | 9/2002 | Snow ........................ 128/203.15 |
| 2003/0140923 A1 * | 7/2003 | Taylor et al. ............. 128/203.12 |
| 2005/0103678 A1 * | 5/2005 | Clark et al. .................... 206/538 |

FOREIGN PATENT DOCUMENTS

| DE | 19805336 A1 | 8/1999 |
| EP | 0796628 A2 | 9/1997 |
| EP | 1106196 A2 | 6/2001 |
| GB | 2340758 A | 3/2000 |
| WO | WO 93/15972 A1 | 8/1993 |
| WO | WO 2004/011070 A1 | 2/2004 |
| WO | WO 2004/041672 A2 | 5/2004 |

* cited by examiner

*Primary Examiner* — Kristen Matter
(74) *Attorney, Agent, or Firm* — Sughrue Mion, PLLC

(57) ABSTRACT

A fluid dispenser device comprising: at least one predosed reservoir (10) that is hermetically sealed and that contains a single dose of powder; an expulsion channel (20) that is terminated by a mouthpiece; and a reservoir opening system (30), each reservoir (10) including a closure layer (12) that is suitable for being pierced and/or torn by said opening system (30) so as to enable the powder that is contained in said reservoir (10) to be expelled through said expulsion channel (20), said reservoir opening system (30) comprising at least two piercer elements (31) that are actuated so as to create at least two distinct openings (25, 26) in said closure layer (12), forming at least one inlet passage (25) for the flow of gas, in particular air, and at least one outlet passage (26) for the powder entrained by said flow of gas, and said device including an inhalation trigger system (50) that creates a flow of gas in said expulsion channel (20) only when a user inhales at or above a predetermined inhalation threshold.

29 Claims, 6 Drawing Sheets

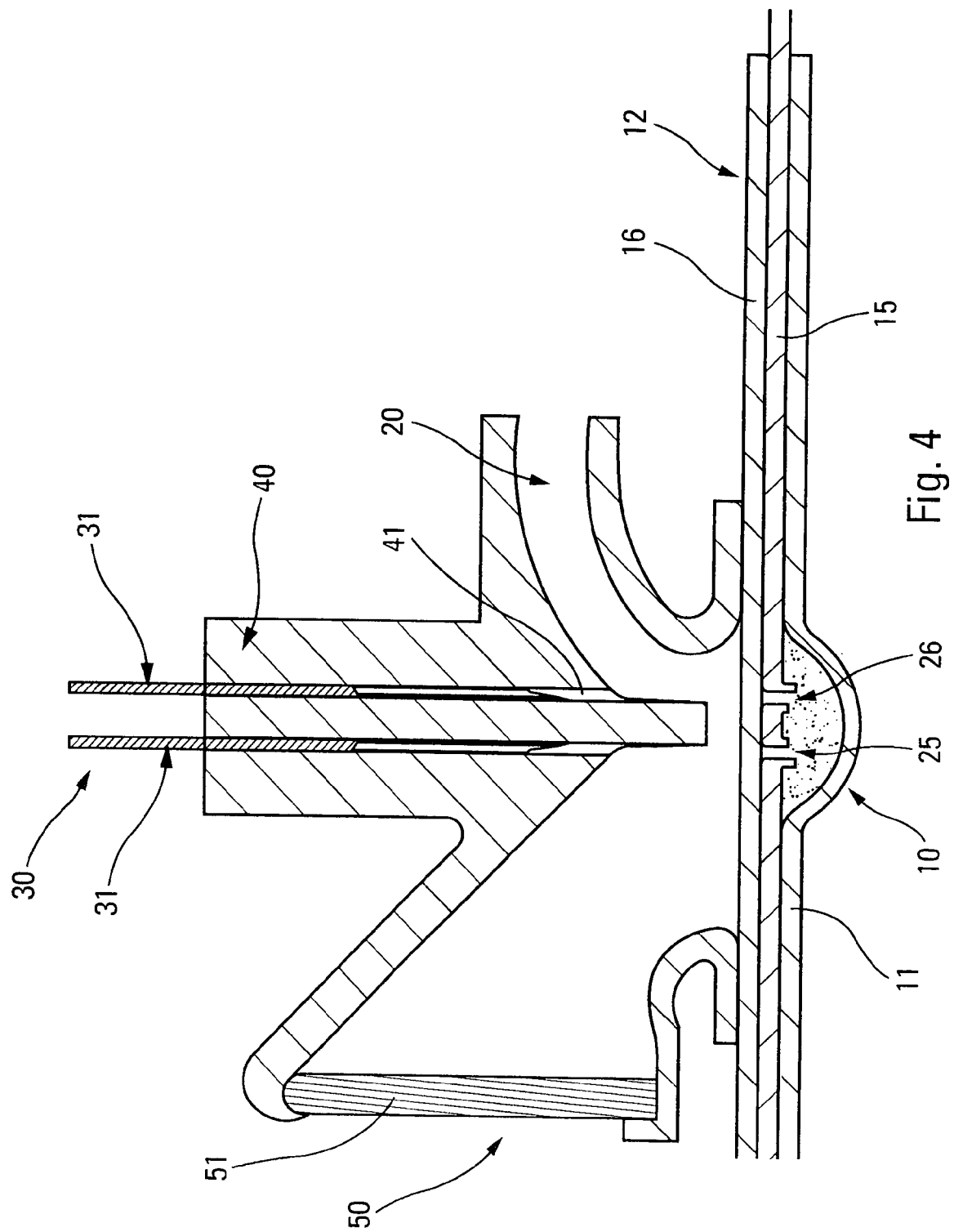

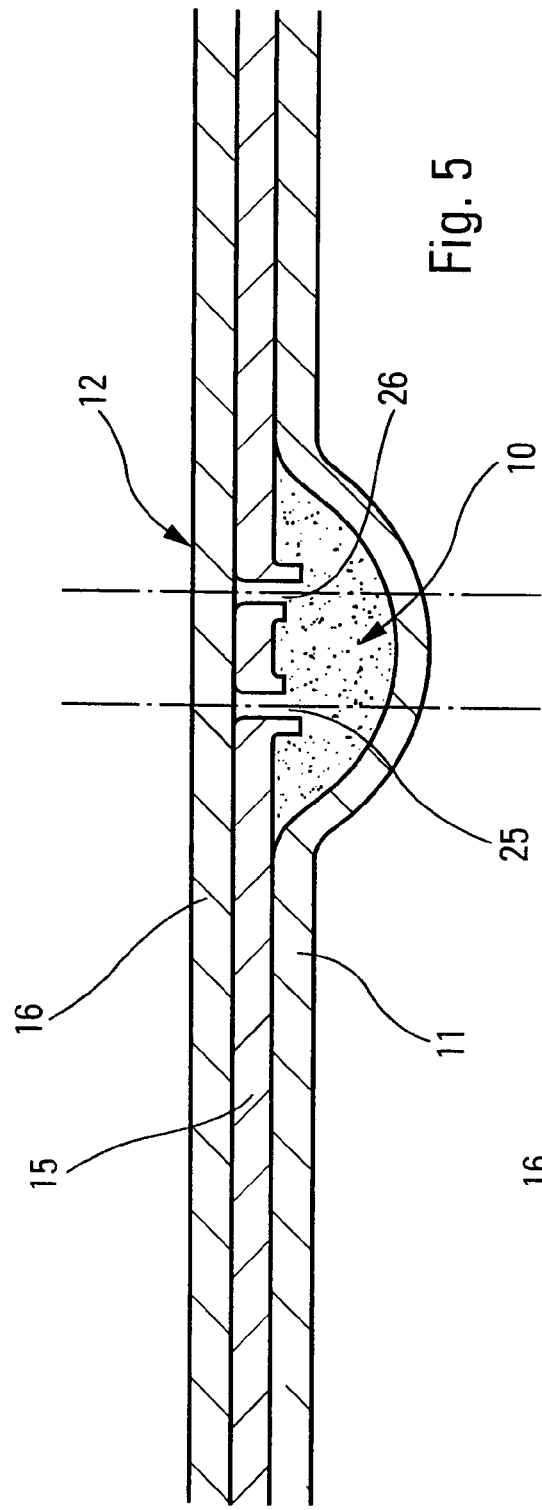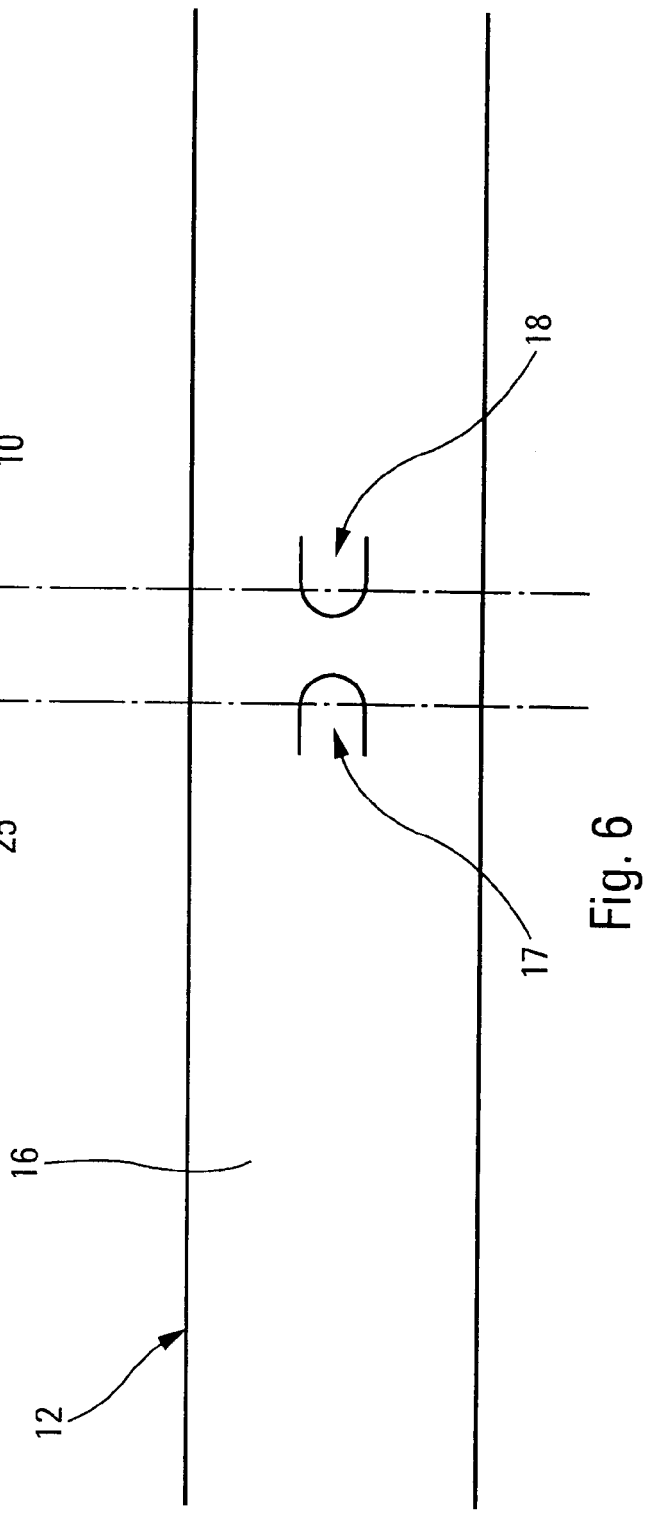

FLUID PRODUCT DISPENSING DEVICE

FIELD OF INVENTION

The present invention relates to a fluid dispenser device, and more particularly to a powder inhaler device.

BACKGROUND

Powder inhaler devices are well known in the state of the art. Some of those devices include a single reservoir containing several doses of powder, and metering means that are adapted to take, on each actuation, one dose of powder for expulsion to the user. Other devices provide individual predosed reservoirs, e.g. blisters, each containing a single dose of powder, each reservoir being opened individually during actuation so as to make it possible to expel the powder contained therein. In the context of a device with one or more predosed reservoirs, different solutions have been proposed for opening the reservoir and accessing its content so as to enable it to be expelled. Thus, it has been proposed to make predosed reservoirs with a peel-off layer, making it possible to expose the reservoir and its powder to a flow of gas, in general air, in order to expel the dose. Other devices provide piercer means for piercing or tearing a portion of the reservoir, thereby also making it possible to expel the content thereof. A problem that can occur with such devices relates to the risk of losing some or all of the doses after opening the reservoir and before inhalation. This reduces metering accuracy and dose reproducibility (underdosing). Another even more serious problem relates to the risk of overdosing. For example, this can occur if, in a device having predosed reservoirs, a reservoir is opened, but the appliance is not used, such that the content of the reservoir is not inhaled. In this event, if the powder is likely to escape from the reservoir and become deposited in portions of the device, then during the next actuation, which will cause another reservoir to open, there is a risk of overdosing. The powder that escaped from the first reservoir could be expelled together with the complete dose from the second reservoir. Depending on the kind of powder, which can be a pharmaceutical, such overdosing risks being very harmful to the user. Another problem that occurs with powder inhaler devices relates to the accuracy and the reproducibility of the metered dose. It can happen that the reservoir or the metering system is not always to be emptied completely on each actuation, thereby generating risks of metering differences from one dose to another, and thus of losing accuracy and reproducibility for the metered dose.

OBJECTS OF THE INVENTION

An object of the present invention is thus to provide a fluid dispenser device that does not have the above-mentioned drawbacks.

In particular, an object of the present invention is to provide a fluid dispenser device that guarantees accurate, reliable, and reproducible dispensing each time the device is actuated.

Another object of the present invention is to provide a fluid dispenser device that guarantees that the entire dose is dispensed on each actuation.

Another object of the present invention is to provide a fluid dispenser device that limits as much as possible, and indeed avoids, any risk of loss of dose after the reservoir has been opened, but before inhalation, and that prevents any risk of overdosing, in particular when a predosed reservoir is opened, but inhalation does not follow.

Another object of the present invention is to provide a fluid dispenser device that prevents any risk of contaminating the fluid to be dispensed.

Another object of the present invention is to provide a fluid dispenser device that is simple and inexpensive to manufacture and to assemble.

The present invention thus provides a fluid dispenser device comprising: at least one predosed reservoir that is hermetically sealed and that contains a single dose of powder; an expulsion channel that is terminated by a mouthpiece; and a reservoir opening system, each reservoir including a closure layer that is suitable for being pierced and/or torn by said opening system so as to enable the powder that is contained in said reservoir to be expelled through said expulsion channel, said reservoir opening system comprising at least two piercer elements that are actuated so as to create at least two distinct openings in said closure layer, forming at least one inlet passage for the flow of gas, in particular air, and at least one outlet passage for the powder entrained by said flow of gas, and said device including an inhalation trigger system that creates a flow of gas in said expulsion channel only when a user inhales at or above a predetermined inhalation threshold.

Advantageously, said piercer elements are displaced simultaneously.

Advantageously, said piercer elements are displaced manually before the user inhales.

Advantageously, said piercer elements are displaceable between a rest position and a piercing position in which they penetrate into a reservoir, said piercer elements being in the piercing position while the dose of powder is being expelled from the reservoir.

Advantageously, each piercer element includes a piercing end that is hollow at least in part, said piercing end forming, in the piercing position, a portion of said expulsion channel through said closure layer.

Advantageously, said piercing end is formed by a hollow point having a longitudinal wall portion that is removed so as to form a longitudinal opening on one side.

Advantageously, said longitudinal opening represents about 20% to about 80% of the periphery of said point.

Advantageously, the longitudinal openings of said piercing ends of two piercer elements are directed away from each other, the closed sides of said piercing ends being disposed facing each other.

Advantageously, the piercing tip of each piercing end is tapering.

Advantageously, the peripheral dimension of the longitudinal opening progressively increases towards said tip.

Advantageously, when the piercer elements are actuated, each piercer element cuts out a respective flap in said closure layer, said flap remaining secured to said closure layer at the open side of each piercing end.

Advantageously, with the exception of said piercing ends, said piercer elements comprise respective bodies that are solid.

Advantageously, said inhalation trigger system comprises a movable valve member in the expulsion channel, upstream from said reservoir, said movable valve member being urged towards a closed position that closes said expulsion channel, and being displaced towards an inhaling position, in which it opens said expulsion channel, enabling a flow of gas to flow towards said reservoir and then towards said mouthpiece of the device, when the user inhales at or beyond said predetermined threshold.

Advantageously, said movable valve member closes the expulsion channel in substantially sealed manner in the closed position.

Advantageously, said device includes a body that defines said expulsion channel at least in part, said body including guide means for guiding said piercer elements.

Advantageously, said body supports said movable valve member.

Advantageously, said device includes a plurality of predosed reservoirs, said device including conveyer means for acting, each time the device is actuated, to convey a respective predosed reservoir to a dispensing position in which it is disposed in the proximity of said expulsion channel and of said opening system, enabling said opening system to be actuated and the user to inhale so as to expel a dose of powder.

Advantageously, said plurality of predosed reservoirs is formed on a single support, such as an elongate strip, a disk, or a cylinder.

Advantageously, in the dispensing position, each predosed reservoir co-operates with said expulsion channel in substantially sealed manner.

Advantageously, said device includes a control member, such as a lid of the device, that is adapted to actuate firstly the reservoir opening system, and secondly said conveyor means.

Advantageously, said expulsion channel, downstream from said predosed reservoir in the gas-flow direction, has a shape that is adapted at least to limit the risk of loss of fluid in the absence of inhalation after the opening system has been actuated.

Advantageously, each predosed reservoir comprises a base layer including a cavity, and a closure layer that is bonded to the base layer so as to seal said cavity hermetically.

Advantageously, said closure layer comprises an inner layer that is made of a material that is powder-tight, air-tight, and moisture-tight, such as a sheet of aluminum, and a protective outer layer that is bonded on said inner layer.

Advantageously, said outer layer is made of a material that has shape memory and that is substantially elastic, such as an elastomer material, so that if the piercer elements of the opening system are actuated, and then returned to their rest position without the powder that is contained in the reservoir having been expelled, the outer layer closes in sealed manner at the flaps that are cut out by said piercer elements, preventing any powder from escaping from said reservoir towards said expulsion channel.

Advantageously, a plurality of predosed reservoirs are formed on a single support that comprises a single base layer provided with a plurality of cavities, and a single closure layer that hermetically seals said plurality of cavities.

The present invention also provides a reservoir kit comprising at least one predosed reservoir that is hermetically sealed and that contains a single dose of powder, each predosed reservoir comprising a base layer forming a cavity, and a closure layer that is bonded to said base layer so as to seal said cavity hermetically, said closure layer comprising an inner layer that is made of a material that is powder-tight, air-tight, and moisture-tight, such as a sheet of aluminum, and a protective outer layer that is bonded on said inner layer.

Advantageously, said outer layer is made of a material that has shape memory and that is substantially elastic, such as an elastomer material, so that if said closure layer is pierced by one or more piercer elements cutting out flaps, and the piercer element(s) are then removed, said outer layer closes in sealed manner at said flaps, preventing any powder from escaping from said reservoir.

Advantageously, a plurality of predosed reservoirs are formed on a single support that comprises a single base layer provided with a plurality of cavities, and a single closure layer that hermetically seals said plurality of cavities.

BRIEF DESCRIPTION OF THE FIGURES

Other characteristics and advantages of the present invention appear more clearly from the following detailed description of an advantageous embodiment thereof, given by way of non-limiting example, and with reference to the accompanying drawings, in which:

FIG. 4 is a view similar to the views in FIGS. 1 to 3, after the reservoir opening system has been actuated and in the absence of subsequent inhalation;

FIG. 5 is a diagrammatic section view of a predosed reservoir as shown in FIG. 4;

FIG. 6 is a plan view of the FIG. 5 reservoir; and

DETAIL DESCRIPTION OF CERTAIN NON-LIMITING EMBODIMENTS OF THE INVENTION

Figure 1:
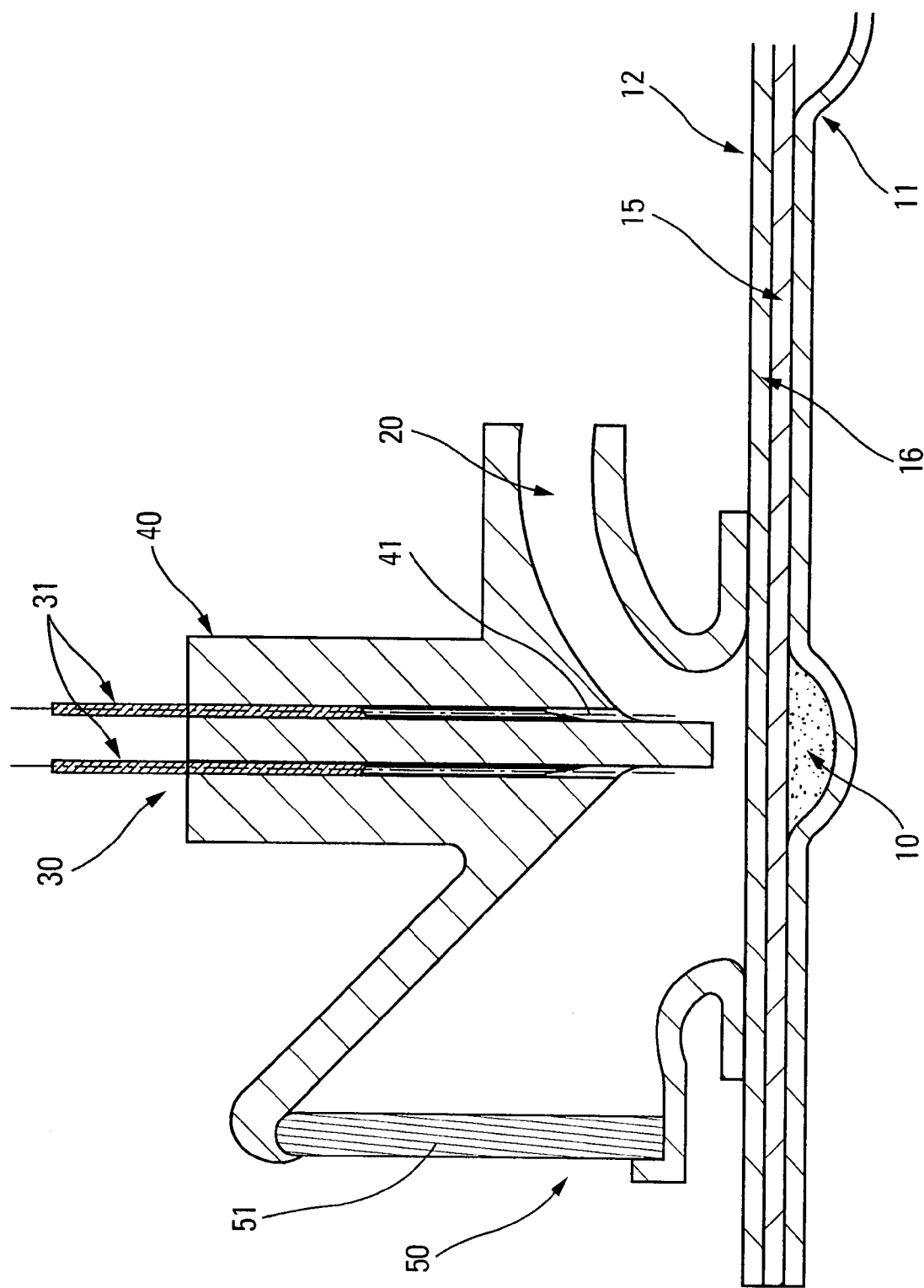
FIG. 1 is diagrammatic section view of a portion of a fluid dispenser device constituting an advantageous embodiment of the present invention, before the reservoir opening system has been actuated and before the user has inhaled.
Figure 2:
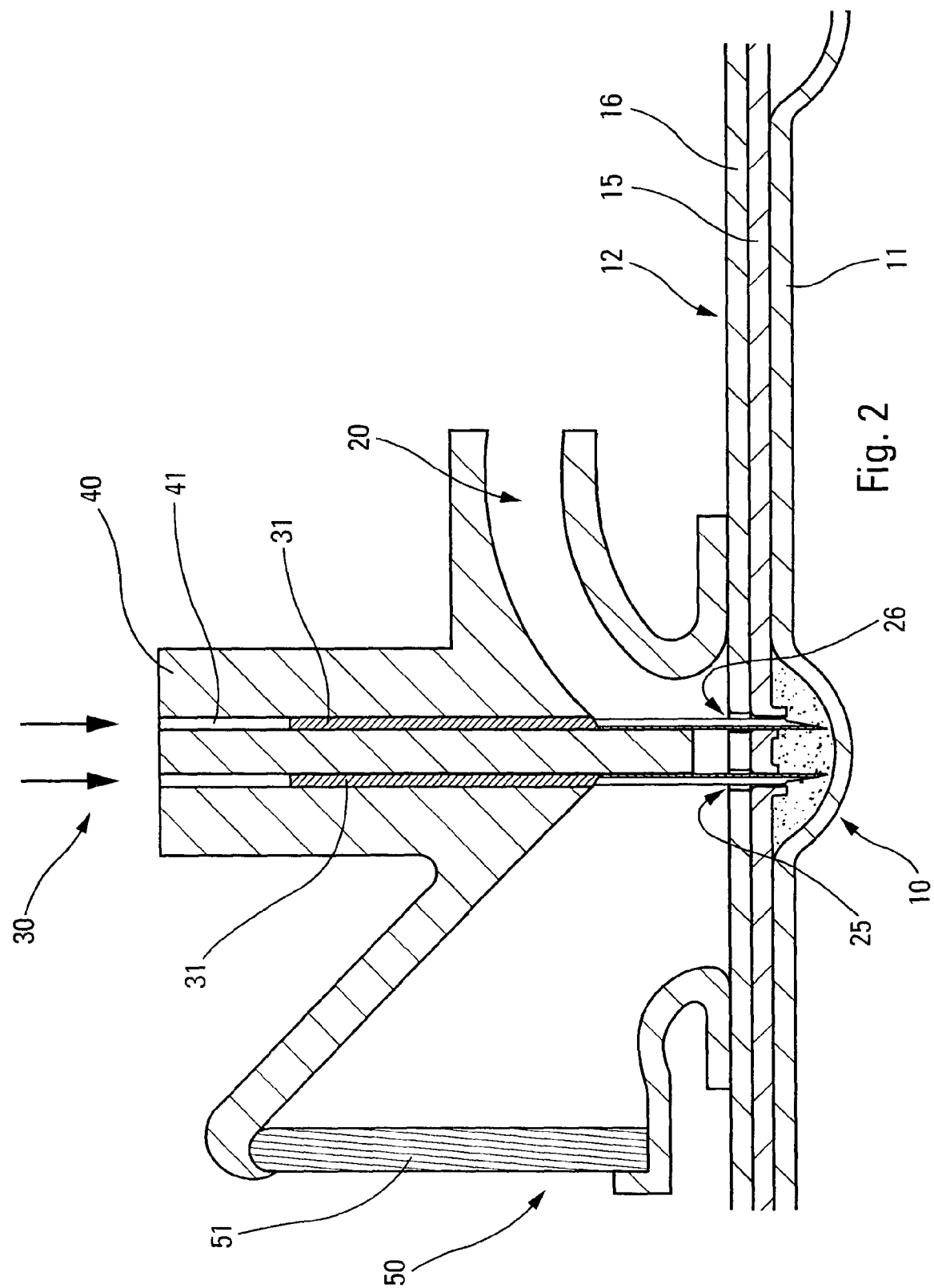
FIG. 2 is a view similar to the view in FIG. 1, after said reservoir opening system has been actuated and before the user has inhaled.

The invention applies more particularly to inhaler devices for inhaling powder, with an advantageous embodiment being described below. However, the present invention is naturally not limited to that type of device, but relates in general to any powder dispenser device.

The inhaler device of the invention includes at least one predosed reservoir 10 that is hermetically sealed and that contains a single dose of powder. The reservoir 10 advantageously includes a base layer 11 forming a cavity that receives the powder. The base layer can be made of aluminum. A closure layer 12 is bonded to said base layer 11, e.g. by adhesive, by heat-sealing, or by any other appropriate bonding means. The closure layer is preferably powder-tight, air-tight, and moisture-tight, and can comprise aluminum. A plurality of predosed reservoirs can be formed on a single support, e.g. in the form of an elongate strip, a disk, or a cylinder. In this event, the single support can comprise a single base layer 11 containing a plurality of cavities, and a single closure layer 12 that hermetically seals said plurality of cavities. Other structures can also be envisaged.

The device further includes an expulsion channel 20 that opens out into a mouthpiece (not shown). A reservoir opening system 30 is provided so as to make it possible to open a predosed reservoir 10 each time the device is actuated.

Advantageously, when the device includes a plurality of predosed reservoirs, the device further includes conveyor means (not shown) that are adapted to bring a respective predosed reservoir 10 into a dispensing position each time the device is actuated so as to enable said reservoir to be opened by the reservoir opening system 30, and so as to enable the powder that it contains to be inhaled through the expulsion channel 20. Advantageously, in the dispensing position, the predosed reservoir 10 co-operates in sealed manner with the expulsion channel 20. The conveyor means can be of any kind, and since they do not participate directly in the invention, they are not described in greater detail below.

In the invention, the opening system 30 comprises at least two piercer elements 31 that are actuated so as to create at least two distinct openings in the closure layer 12 of the predosed reservoir 10. The following description is made with reference to two piercer elements 31, but naturally there can be more of them, e.g. three or four. The piercer elements are preferably displaced manually and simultaneously, as shown in FIGS. 1 to 4. In particular, the piercer elements can be displaceable between a rest position, shown in FIGS. 1 and 4, and a piercing position, shown in FIGS. 2 and 3, said piercer elements preferably being in the piercing position while the dose of powder is being expelled from the predosed reservoir. In fact, the piercing end of each piercer element 31 preferably forms a portion of the expulsion channel 20 during expulsion. The opening system 30 is advantageously actuated by means of a control member (not shown) that can be a lid or a protective cap of the device. Thus, the piercer elements 31 can be displaced towards their piercing positions while the cap is being opened and can be returned towards their rest positions while said cap is being closed.

With reference more precisely to FIGS. 1 to 4, it should be observed that, in the dispensing position, the predosed reservoir 10 co-operates with an upstream portion of the expulsion channel 20 that is situated upstream from the reservoir 10, and with a downstream portion of the expulsion channel 20 that is disposed downstream from said reservoir. During inhalation, and under the conditions that are described below, a flow of gas, in particular air, is created through said expulsion channel 20, the flow of gas flowing from the upstream portion of the expulsion channel. The flow can then penetrate inside the predosed reservoir 10 through at least one inlet opening 25 that is formed by at least one of the piercer elements 31. The flow of gas thus mixes with the powder that is contained in the reservoir, and the mixture is expelled through at least one outlet opening that is formed by at least one other piercer element 31, the mixture thus flowing into the downstream portion of the expulsion channel 20 towards the mouthpiece (not shown). This sequence is shown diagrammatically in FIG. 3, arrow A1 showing the flow of gas in the upstream portion of the expulsion channel, arrow A2 showing the path of the flow of gas inside the predosed reservoir 10, and arrow A3 showing the flow of gas and powder being displaced towards the mouthpiece.

Figure 3:
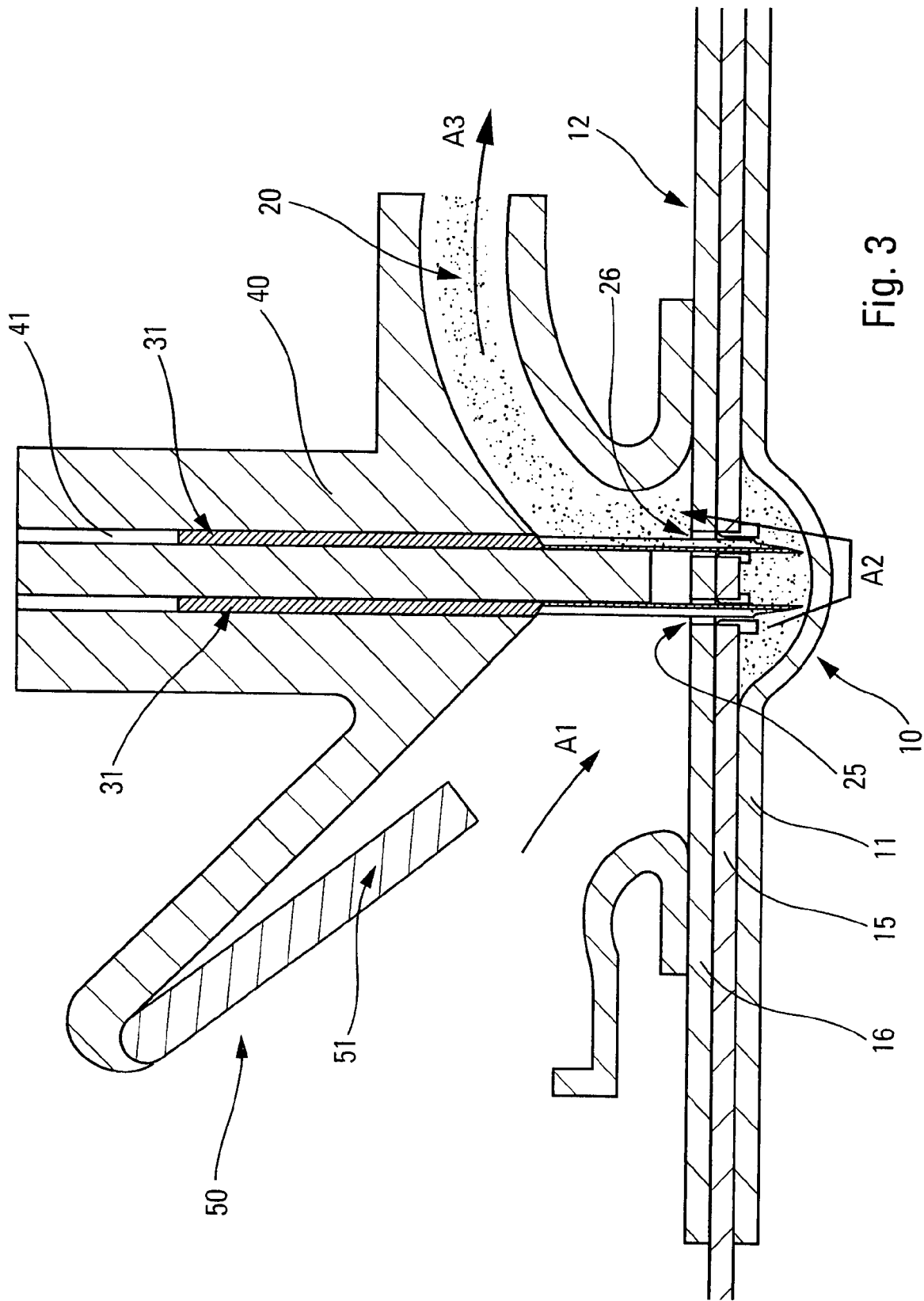
FIG. 3 is a view similar to the views in FIGS. 1 and 2, while the user is inhaling.

In the invention, the dispenser device also includes an inhalation trigger system 50. The inhalation trigger system 50 advantageously comprises a valve member 51 that is displaceable between a closed position and an inhaling position. In the closed position shown in FIGS. 1, 2, and 4, the movable valve member 51 closes the upstream portion of the expulsion channel 20, with said upstream portion preferably being closed in sealed manner. Preferably, the movable valve member 51 is urged towards its closed position by any means, e.g. gravity, or separate means such as a spring. The movable valve member 51 is adapted to be displaced towards its inhaling position when the user inhales at or above a predetermined threshold suction level. So long as the user does not inhale deeply enough in order to reach the threshold, the movable valve member 51 remains closed and no flow of gas can propagate into the expulsion channel 20, such that the powder cannot be expelled from the reservoir 10. When the user reaches the predetermined threshold suction level, the movable valve member 51 opens, e.g. pivots as shown in FIG. 3, thereby allowing a flow of gas, in particular air, to be created that causes the powder to be expelled as explained above.

Thus, while the powder is being expelled, the piercer elements 31 are preferably in their piercing position, in which they penetrate into the predosed reservoir 10, through the closure layer 12. In this position, if the user agitates or moves the device, the risks of powder being lost are almost non-existent. The specific shape of the piercer elements 31 makes it almost impossible for any powder to escape. It could also be envisaged that the expulsion channel is of a shape that is specifically adapted to reduce still further any risk of dose being lost. For example, deflectors or bent portions could be provided that would retain possible losses of powder in the channel, such that, during inhalation, the entire dose would still be dispensed. The invention thus makes it possible to limit, to a significant degree, any risk of loss of dose (underdosing) after the reservoir has been opened and before inhalation takes place.

During inhalation, the flow of gas is powerful enough to guarantee that the predosed reservoir 10 is totally and completely emptied, because of the minimum predetermined threshold that the user must reach in order to cause the movable valve member 51 to open. The invention thus makes it possible to guarantee complete and total emptying, and thus enables the metered dose to be accurate and reproducible on each actuation.

The device advantageously includes a body 40 that defines the expulsion channel 20 at least in part. The body 40 can further include guide means 41 for guiding the piercer elements 31 of the opening system 30. Advantageously, the body 40 also forms the support for the movable valve member 51. Finally, in the dispensing position of the predosed reservoir, the body 40 advantageously co-operates in sealed manner with said reservoir, thereby guaranteeing reliable, total, complete, and reproducible expulsion on each actuation. This embodiment makes it possible to simplify the manufacture and the assembly of the device, and therefore to reduce the cost thereof in non-negligible manner.

Figure 7:
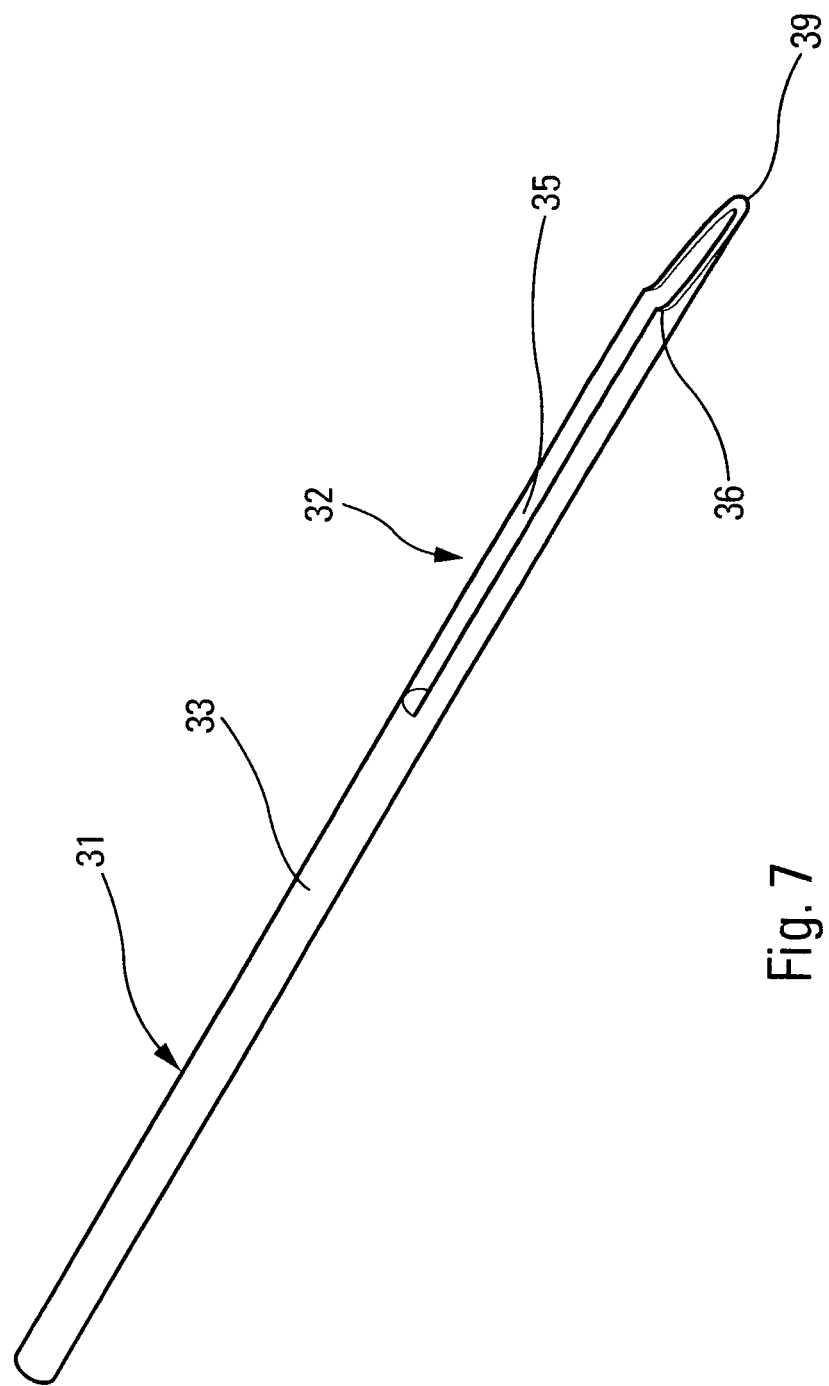
FIG. 7 is a detailed view of a piercer element of the device shown in FIGS. 1 to 4.

With reference more particularly to FIG. 7, which is a detailed view of a piercer element 31, it should be observed that the piercer element 31 comprises a solid body portion 33 and a piercing end 32 that is hollow at least in part. It is the piercing end 32 that forms a portion of the expulsion channel 20 in the piercing position. To do this, the piercing end 32 is advantageously made in the form of a hollow point having a longitudinal wall portion that is cut out or removed so as to form a longitudinal opening 35 on one side of said end. The example shown in FIG. 7 shows an opening 35 that forms about one third of the periphery of the point, but naturally the opening could have dimensions that are greater or smaller than the dimensions shown. For example, the longitudinal opening could represent about 20% to about 80% of the periphery of the point. In addition, the tip of the piercing end 39 is preferably tapering, so as to make it possible to pierce cleanly and accurately. Advantageously, the peripheral dimension of the longitudinal opening 35 can also be modified at said tip 39, e.g. progressively increased towards said tip. The tapering portion that forms the tip 39 of the piercing end 32 advantageously forms a slope that makes it possible to make a progressive and accurate cut as the piercer element penetrates into the reservoir 10 through the closure layer 12. Advantageously, a shoulder 36 can be provided at the junction between the slope of the tip 39 and an edge of the longitudinal opening 35, so as to improve pivoting of the flap 17, 18 cut out by the piercer element 31 in the closure layer 12. FIG. 6 diagrammatically shows a plan view of the closure layer 12, and shows the two flaps 17, 18 that are formed by the two piercer elements 31. It should be observed that the flaps 17, 18 remain secured to the closure layer 12 at the open side 35 of each piercer element 31. The piercer elements 31 are advantageously identical, but differences could also be envisaged between the piercer element(s) forming the inlet passage(s) 25, and the piercer element(s) forming the outlet passage(s) 26, e.g. concerning certain dimensions.

The open sides 35 of the two piercer elements 31 are advantageously directed away from each other, thereby signifying that the closed sides of the piercing ends 32 are facing each other. This configuration improves the directing of the flow of gas towards the inside of the reservoir, and its expulsion therefrom together with the powder. The piercing end 32 advantageously extends along the piercer element 31 over a distance such that, in the piercing position (shown in FIG. 2), the edge of the piercing end 32 remote from the tip 39 co-operates with the body 40, thus further encouraging the flow of gas.

In a particularly advantageous aspect, the predosed reservoir 10 can include a closure layer 12 of complex structure. As described above, the reservoir 10 can be formed by a base layer 11, e.g. made of aluminum, that includes the cavity(ies) containing the powder. The closure layer 12 thus includes an inner layer 15 that is made of a material that is powder-tight, air-tight, and moisture-tight, preferably aluminum. The inner layer 15 is bonded on the base layer 11 in any appropriate way so as to seal the cavity(ies) hermetically. The closure layer further includes an outer layer 16 that is bonded to said inner layer 15, also in any appropriate way. The outer layer 16 is a protective layer that is preferably made of a material that is relatively flexible and that has shape memory, such as an elastomer material. The advantage of this structure is that when the opening system is actuated, and when the piercer elements 31 come to pierce the closure layer 12, passages are created between the expulsion channel 20 and the inside of the reservoir 10. If the user returns the opening system 30 to the rest position, i.e. causes the piercer elements 31 to retract from the reservoir 10 so as to return them to their respective rest positions, the protective outer layer 16 closes in sealed manner so as to prevent any loss of powder from the reservoir. This can occur if the user opens the protective cap of the inhaler and then closes it without inhaling, for example. Although the aluminum inner layer 15 remains torn, and an opening is thus likely to remain at this location, the protective outer layer 16 closes by means of its elasticity, thus closing the reservoir 10, preferably in such a manner as to be at least powder-tight. This is particularly advantageous in order to avoid the risk of overdosing. When there is no protective outer layer, in the event that the user opens the reservoir and then causes the opening system to retract without inhaling, a potential risk can exist of the powder that is contained in the open reservoir escaping into the expulsion channel, the powder then being dispensed during the next actuation together with the complete dose of the next predosed reservoir. For pharmaceuticals, such overdosing can be very harmful, and the invention makes it possible to avoid this risk effectively and at low cost. Naturally, the presence of the protective outer layer 16 also makes it possible to avoid any risk of loss of dose or of underdosing in particularly effective manner.

It should be noted that this particular structure of closure layer 12, with its protective outer layer, could be implemented independently of the above-described inhaler device, and, in particular, independently of the trigger system. In addition, such a protective outer layer could also be effective with systems that include any number of piercer elements, namely a single piercer element or a plurality of piercer elements.

It should be noted that although the invention is described above with reference to a particular embodiment thereof, it is not limited to the examples shown. Thus, the shape of the reservoir can be any shape. In addition, the materials described are given only by way of example, and other materials can be envisaged. In addition, the invention is described with reference to using two piercer elements 31. Naturally, three or more such piercer elements could be used in the ambit of the present invention. In particular, it is possible to envisage a single piercer element for forming the inlet opening of the reservoir, and two piercer elements in order to form the outlet. In addition, the piercer elements are not necessarily identical, and the piercer element that forms the outlet opening of the reservoir could have different dimensions, in particular greater dimensions, than the piercer element that forms the inlet opening. In addition, the structure of the inhalation trigger system can be of any kind, the shape of the valve member 51 not being limiting.

Other modifications can also be envisaged without going beyond the ambit of the present invention, as defined by the accompanying claims.

The invention claimed is:

1. A fluid dispenser device comprising: at least one predosed reservoir that is hermetically sealed and that contains a single dose of powder; an expulsion channel; and a reservoir opening system, each reservoir including a closure layer that is suitable for being pierced and/or torn by said opening system so as to enable the powder that is contained in said reservoir to be expelled through said expulsion channel, wherein said reservoir opening system comprises at least one piercer element that is actuated so as to create at least one opening in said closure layer, forming at least one inlet passage for the flow of gas, and at least one outlet passage for the powder entrained by said flow of gas, and said device includes an inhalation trigger system that creates a flow of gas in said expulsion channel only when a user inhales at or above a predetermined inhalation threshold, each predosed reservoir comprising a base layer including a cavity and the closure layer that is bonded to the base layer so as to seal said cavity hermetically, said closure layer comprising an inner layer that is made of a material that is powder-tight, air-tight, and moisture-tight, and a protective outer layer that is bonded on said inner layer, said outer layer is made of a material that has shape memory and that is substantially elastic, so that if the at least one piercer element of the opening system is actuated, and then returned to its rest position without the powder that is contained in the reservoir having been expelled, the outer layer closes in sealed manner at a flap that is cut out by said at least one piercer element, preventing any powder from escaping from said reservoir towards said expulsion channel; and wherein the inner layer for the closure layer seals the cavity.

2. A device according to claim 1, in which said device comprises at least two piercer elements forming the at least one inlet passage for the flow of gas, the and at least one outlet passage for the powder entrained by said flow of gas, said piercer elements being displaced simultaneously.

3. A device according to claim 2, in which said device includes a body that defines said expulsion channel at least in part, said body including guide means for guiding said piercer elements.

4. A device according to claim 3, in which said body supports said movable valve member.

5. A device according to claim 2, in which said piercer elements are displaced manually before the user inhales.

6. A device according to claim 2, in which said piercer elements are displaceable between a rest position and a piercing position in which they penetrate into a reservoir, said piercer elements being in the piercing position while the dose of powder is being expelled from the reservoir.

7. A device according to claim 6, in which each piercer element includes a piercing end that is hollow at least in part, said piercing end forming, in the piercing position, a portion of said expulsion channel through said closure layer.

8. A device according to claim 7, in which, with the exception of said piercing ends, said piercer elements comprise respective bodies that are solid.

9. A device according to claim 7, in which said piercing end is formed by having a longitudinal wall portion that is removed so as to form a longitudinal opening on one side.

10. A device according to claim 9, in which, when the piercer elements are actuated, each piercer element cuts out a respective flap in said closure layer, said flap remaining secured to said closure layer at an open side of each piercing end where there is the longitudinal opening.

11. A device according to claim 9, in which said longitudinal opening represents about 20% to about 80% of the periphery of said piercing end.

12. A device according to claim 9, in which the longitudinal openings of said piercing ends of the two piercer elements are directed away from each other, closed sides of said piercing ends being disposed facing each other.

13. A device according to claim 9, in which a piercing tip of each piercing end is tapering.

14. A device according to claim 9, in which the size of the longitudinal opening progressively increases towards a tip of the piercing end.

15. A device according to claim 1, in which said inhalation trigger system comprises a movable valve member in the expulsion channel, upstream from said reservoir, said movable valve member being urged towards a closed position that closes said expulsion channel, and being displaced towards an inhaling position, in which it opens said expulsion channel, enabling a flow of gas to flow towards said reservoir and then towards said mouthpiece of the device, when the user inhales at or beyond said predetermined threshold.

16. A device according to claim 15, in which said movable valve member closes the expulsion channel in substantially sealed manner in the closed position.

17. A device according to claim 1, including a plurality of predosed reservoirs, wherein, each time the device is actuated, a respective predosed reservoir is conveyed to a dispensing position in which it is disposed in the proximity of said expulsion channel and of said opening system, enabling said opening system to be actuated and the user to inhale so as to expel a dose of powder.

18. A device according to claim 17, in which said plurality of predosed reservoirs is formed on a single support.

19. The device according to claim 18, wherein the single support is an elongate strip, a disk, or a cylinder.

20. A device according to claim 17, in which, in the dispensing position, each predosed reservoir co-operates with said expulsion channel in a substantially sealed manner.

21. A device according to claim 1, in which said expulsion channel, downstream from said predosed reservoir in the gas-flow direction, has a shape that is adapted at least to limit the risk of loss of fluid in the absence of inhalation after the opening system has been actuated.

22. A device according to claim 1, in which a plurality of predosed reservoirs are formed on a single support that comprises a single base layer provided with a plurality of cavities, and a single closure layer that hermetically seals said plurality of cavities.

23. The fluid dispenser device according to claim 1, wherein the inner layer is made of a sheet of aluminum.

24. The fluid dispenser device according to claim 1, wherein the outer layer is made of an elastomer material.

25. A reservoir kit comprising at least one predosed reservoir that is hermetically sealed and that contains a single dose of powder, each predosed reservoir comprising a base layer forming a cavity, and a closure layer that is bonded to said base layer so as to seal said cavity hermetically, the reservoir kit being characterized in that said closure layer comprises an inner layer that is made of a material that is powder-tight, air-tight, and moisture-tight, and a protective outer layer that is bonded on said inner layer, said protective outer layer being made of a material that has shape memory and that is substantially elastic; and wherein the inner layer for the closure layer seals the cavity.

26. A reservoir kit according to claim 25, in which said outer layer is made of a material that has shape memory and that is substantially elastic, so that if said closure layer is pierced by one or more piercer elements cutting out flaps, and the one or more piercer elements are then removed, said outer layer closes in sealed manner at said flaps, preventing any powder from escaping from said reservoir.

27. The reservoir kit according to claim 26, wherein the outer layer is made of an elastomer material.

28. A reservoir kit according to claim 25, in which a plurality of predosed reservoirs are formed on a single support that comprises a single base layer provided with a plurality of cavities, and a single closure layer that hermetically seals said plurality of cavities.

29. The reservoir kit according to claim 25, wherein the inner layer is made of a sheet of aluminum.

\* \* \* \* \*